United States Patent [19]
Halliday et al.

[11] Patent Number: 5,388,136
[45] Date of Patent: Feb. 7, 1995

[54] X-RAY INSPECTION APPARATUS FOR ELECTRONIC CIRCUITS

[75] Inventors: David K. Halliday, Greenock; Colin D. McCall; Alexander S. McKinnon, both of Gourock; Christopher D. Smith, Glasgow, all of Scotland

[73] Assignee: International Business Machines Corporation, Armonk, N.Y.

[21] Appl. No.: 65,010

[22] Filed: May 24, 1993

[30] Foreign Application Priority Data

Jul. 3, 1992 [GB] United Kingdom ................ 9214114

[51] Int. Cl.⁶ ............................................. G01N 23/04
[52] U.S. Cl. ...................................... 378/58; 378/21; 378/22
[58] Field of Search ........................ 378/21, 22, 23, 24, 378/25, 58, 62

[56] References Cited

U.S. PATENT DOCUMENTS

| | | | |
|---|---|---|---|
| 2,207,867 | 7/1940 | Loebell | 378/23 |
| 3,746,872 | 7/1973 | Ashe et al. | 378/21 X |
| 3,818,220 | 6/1974 | Richards | 378/23 |
| 4,139,776 | 2/1979 | Hellstrom | 378/22 X |
| 4,926,452 | 5/1990 | Baker et al. | 378/22 |

FOREIGN PATENT DOCUMENTS 236001  9/1987  European Pat. Off. .

Primary Examiner—David P. Porta
Attorney, Agent, or Firm—Charles W. Peterson, Jr.

[57] ABSTRACT

An X-ray computerized system for programmable, high-resolution X-ray inspection of manufactured electronic circuits. Such a system comprises: means for directing X-rays to produce X-ray images representing illuminations of circuit elements from different angles; and detecting means for detecting said images, said detecting means comprising a plurality of detectors, each of said detectors positioned to intercept X-rays after passing through a circuit element from a particular associated angle of illumination.

7 Claims, 3 Drawing Sheets

X-RAY INSPECTION APPARATUS FOR ELECTRONIC CIRCUITS

This invention relates to a computerised system for programmable, high resolution X-ray inspection of manufactured electronic items.

The reduced size of electronics components and the consequent increased density of items on printed circuit boards, has caused the traditional ways of inspection to be no longer sufficient for an affordable and precise quality control inspection. Especially in those cases where a Direct Chip Attached (DCA) technology is used, in which the solder connections are hidden from view, fast accurate quality control inspection of the electronic devices is very difficult.

It is known to use penetrating radiation to inspect electronic items by producing images of the internal structure of the devices and the connections. Most of the existing inspection systems use X-ray radiations and radiographic techniques.

European Patent EP0236001 describes a machine for inspecting solder connections on printed circuit boards using digital X-ray radiographic techniques. Though the inspections performed with this machine are quite satisfactory in many situations, there are cases where some relevant characteristics of a solder connection are masked by other neighbouring objects.

An improvement to this technique is provided by the system disclosed in the U.S. Pat. No. 4,926,452. This system utilises a rotating X-ray beam combined with a rotating detector to produce cross-sectional images of the printed circuit board to be inspected. Such a system performs an automated inspection using high resolution images.

However this system has some disadvantages, partly due to the heavy rotating mass of the detector and partly due to the way the inspection is performed.

The continual image laminography, obtained by this system, is able to cover a wide range of devices; however it cannot remove dense shadows from any image angle that may cause problems in the total laminograph image.

The modification of the parameters (e.g. the angle of incidence of the X-ray radiation) is not readily available without losing the magnification.

For example for a DCA printed circuit board a high angle inspection of up to 50 Deg.) could be required; with the U.S. Pat. No. 4,926,452 only low angles (less than 30 Deg.) are available. Also with this system only one kind of analysis (the laminography inspection) is possible. In many cases it would be very useful for the user to be able to vary such parameters dynamically or even to combine different kinds of inspection (e.g. laminography and transmissive inspection together).

It is therefore an object of the present invention to overcome the above drawbacks of the prior art.

According to the present invention we provide a X-ray inspection apparatus for electronic circuits comprising:
means for directing X-rays to product X-ray images representing illuminations of circuit elements from different angles; and detecting means for detecting said images; said inspection apparatus being characterised in that said detecting means comprises a plurality of detectors, each of said detectors positioned to intercept X-rays after passing through a circuit element from a particular associated angle of illumination.

Such an apparatus avoids the bulky rotating mass of the detector of the prior art and permits different kinds of inspection. Also parameters such as the angular incidence of the X-ray radiation or the distance of the source and the detector from the inspected board are dynamically adjustable without losing the magnification (even for high angle of incidence).

The foregoing and other objects, features, and advantages of the invention will be apparent from the following more particular description of the preferred embodiment of the invention, as illustrated in the accompanying drawings.

Figure 1:
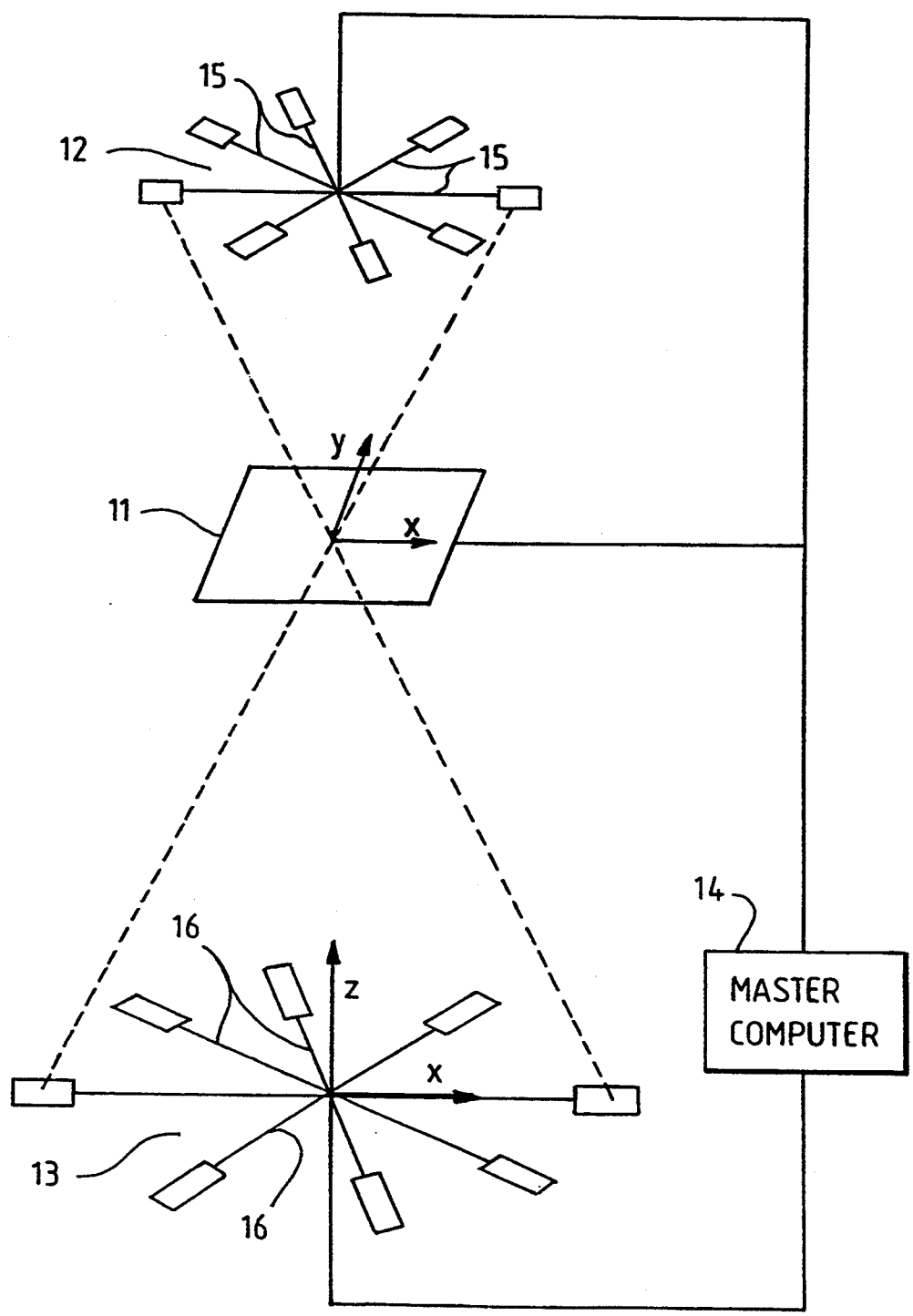
FIG. 1 is a schematic diagram of the system of the preferred embodiment.

In FIG. 1 the whole system is shown. The electronic device to be inspected is loaded on to a table set (11) which is positioned between the X-ray sources (12) and the X-ray detectors (13). The table set (11) can move in the plane where it lies, and its movement is controlled by a master computer (14).

The system includes a plurality of X-ray sources. In the preferred embodiment there are eight such sources which are positioned in a radial pattern in a plane. Each source is mounted on a radially movable slide (15), which has a computer controlled positioning system. The movement of each source is controlled by the master computer (14). Each source, in the preferred embodiment, is rated at 160 KVA at 1.0 mA.

The system includes a plurality of X-ray detectors there being the same number of detectors as sources. In the preferred embodiment there are eight such detectors; they are positioned in a radial pattern in a plane which is parallel to the plane in which the X-ray sources (12) lie. Each detector is mounted on a radially moving slide, (16) which has a computer controlled positioning system. The movement of each source is controlled by the master computer (14).

In the preferred embodiment each detector has a Silicon Intensified Target (SIT) image detector flat plate phosphor detector design, feeding through parabolic correction to inline convolution smoothing and finally to standard image board capture technology and computerised algorithm manipulation. Each image board includes a 1024×1024 video RAM. The operation of such parabolic correction, inline convolution smoothing and image board capture technology will be well understood by those skilled in the art and will not be described further herein. Each detector is positioned to intercept X-rays after passing through the electronic device and each detector is associated with a particular angle of illumination.

The synchronisation between the sources and the detectors is controlled by the master computer (14). Such control is done by computerised radial mapping of the source/detector to generate an offset table.

All the image from the detectors will be offset by the radial mapping coordinates when entering nay video RAM. The video RAM will be larger than the video size (i.e. an image of 512×512 will be sent to a video RAM size 1024×1024 at a starting offset applicable to the data generated by the radial mapping offset table). This offset system will allow any detector to use any video RAM that is free of workload, and speed the data accordingly.

Figure 2:
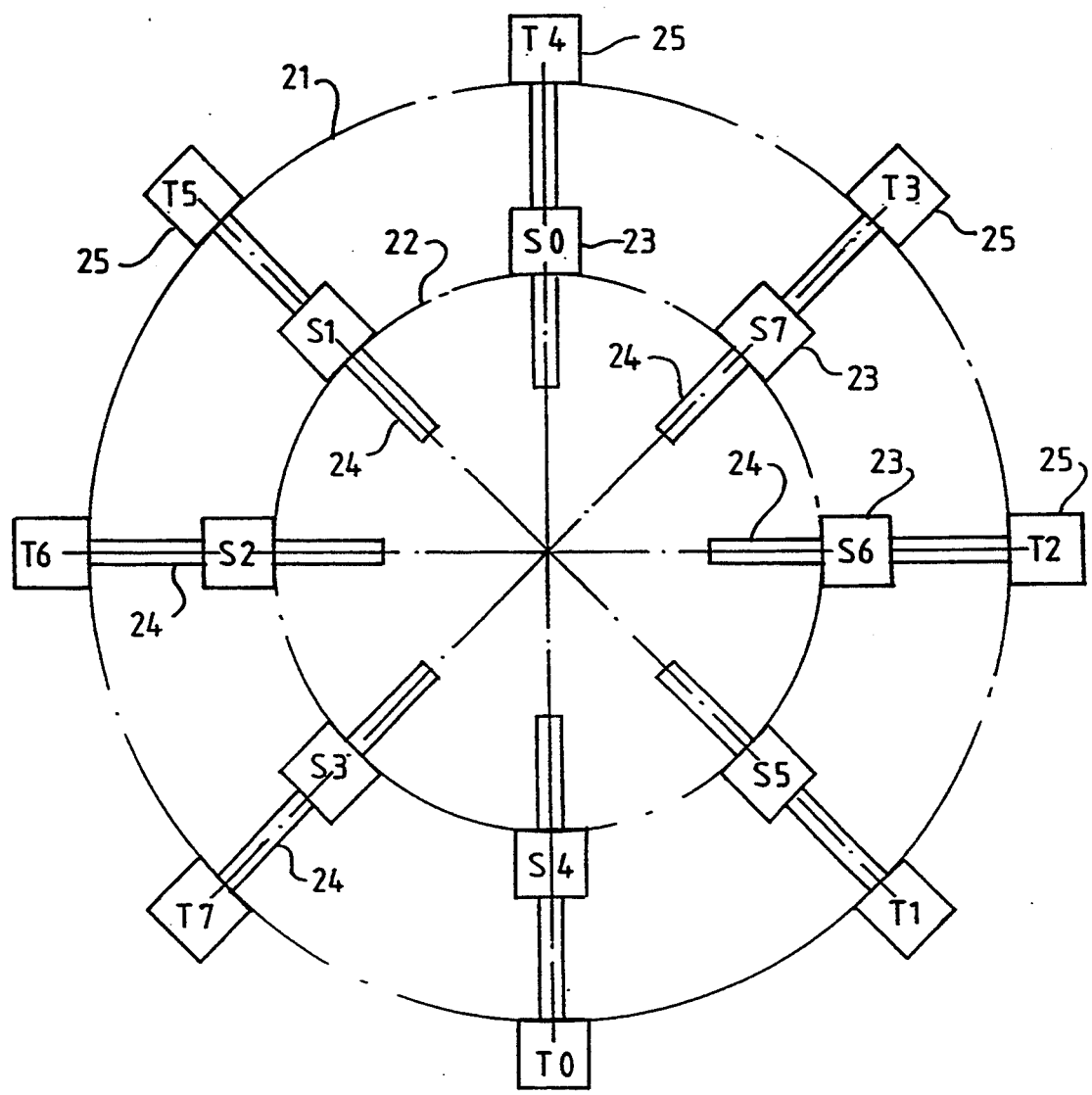
FIG. 2 is a schematic diagram of the multiple sources and multiple detectors disposition.

In FIG. 2 an example of positioning of the sources and detectors is represented. The view is a top-view perpendicular to the planes on which the sources and the detectors lies. The two circles (21 and 22) are parallel and on opposite sides with respect to the electronic item to be inspected. On the inner circle (22) eight X-ray sources (23) are mounted on independent adjusting screws (24), which allow the sources to move in a radial direction.

Figure 3:
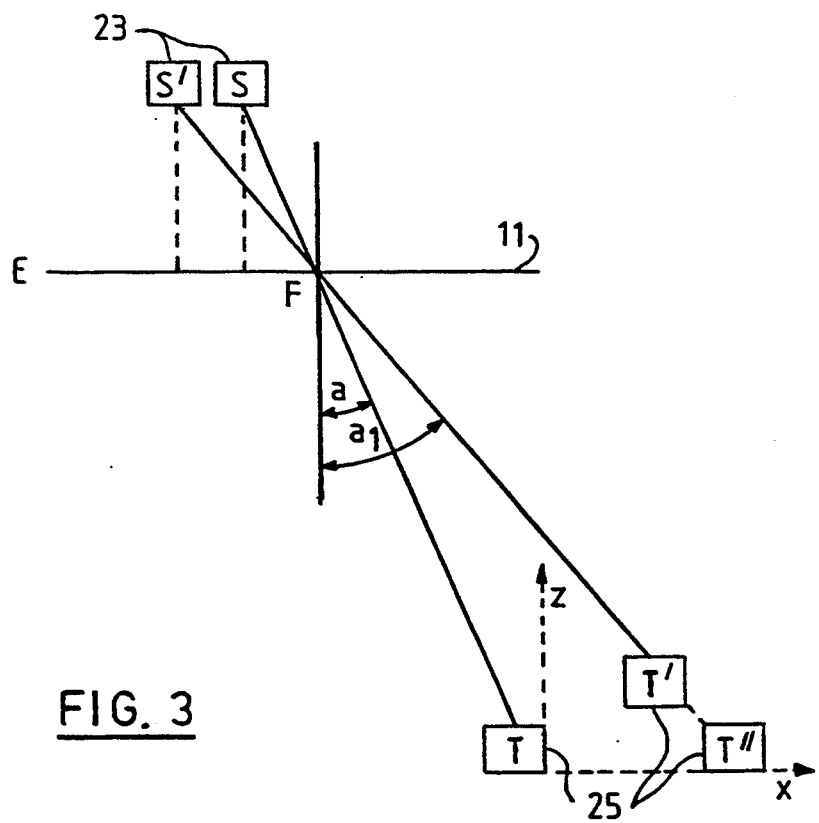
FIG. 3 is an example of the way the angle of inspection can change without changing the magnification.

The same movement is permitted to the eight X-ray detectors (25) which are represented in FIG. 3 on the outer circle. Another movement is permitted to both the sources and the detectors in an orthogonal directions with respect to the circles. All the movements are controlled by the master computer (14). Said master computer (14) also controls the correspondence between each source and the associated detector.

The circular pattern in which the sources and the detectors are disposed is only one of the possible ways of positioning them.

This freedom of movement in the radial and orthogonal directions represents one of the advantages of the present invention. Referring to FIG. 3, if we want to change the angle of inspection of the electronic circuit from a smaller angle 'a' to a bigger angle 'a1', we have to keep constant the distance between the source and the detector. If this is omitted the magnification changes. The magnification is the ratio of the distance ST between the source (23) and its associated detector (25) to the distance SF between the source (23) and the Focus point F on the inspection object (11).

If we want SE to remain constant, ST would increase if the detector is not moved in the orthogonal direction z, but only on the plane direction x. With this system the detector can be moved from the position T to the position T1 keeping constant the distance between the source (23) and the detector (25) and consequently the magnification ratio ST/SF.

To realise a cross-sectional image, the information is gathered from eight 45 Deg. offset source/detectors to eight image boards, each image board corresponding to one source/detector and having a video RAM. Referring to FIG. 2 the source S0 (23) has to be combined with the detector T0 (25), the source S1 with the detector T1 and so on. The eight images will be combined with a logical 'AND' on a certain grey level value to a master video RAM (any of the eight) to give an image similar to tomographic images. This technique will smear out all unwanted data in the individual images and highlight the in-focus data. To resolve the lack of continuity of this system with respect to the continual rotation acquisition laminography a convolution process to smooth the differences between the discrete images is performed. A further advantage of this system is that any source/detector image that is unwanted can be omitted, with the rest of the source detector images only being logically 'ANDed' together.

If a direct transmissive image is required a source has to be aligned with one of the detectors; for example the source S4 (23) and the detector T0 (25) could be aligned to produce a 90 Deg. image without smoothing.

Figure 4:
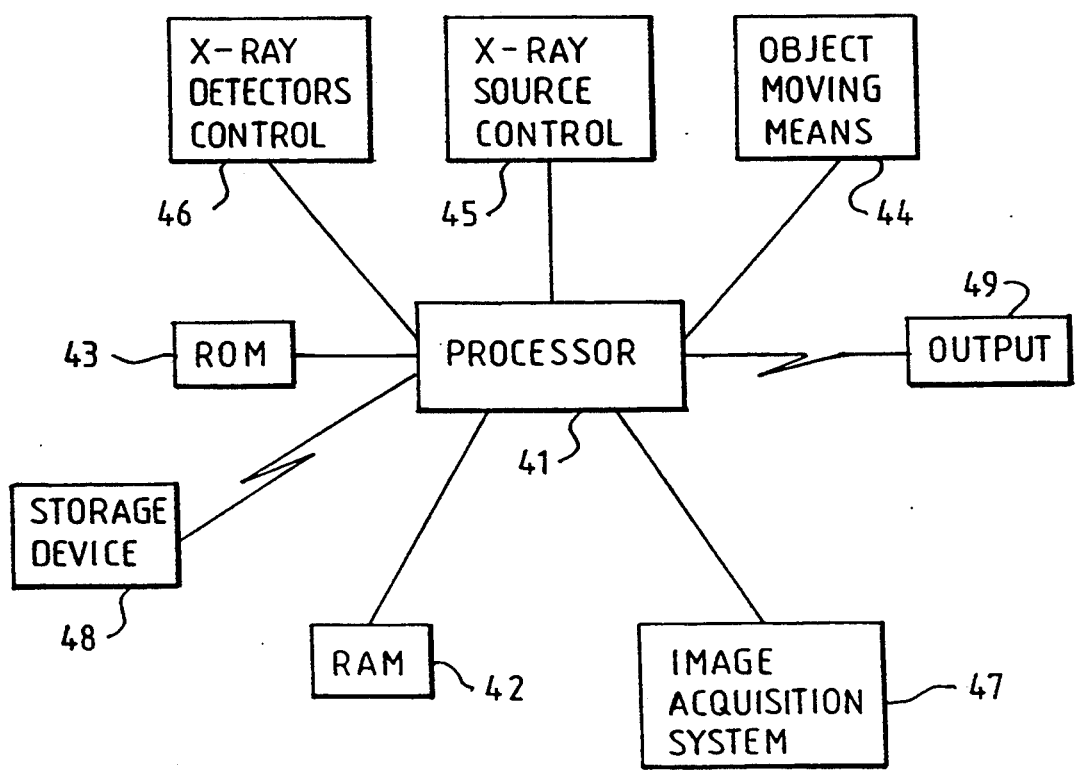
FIG. 4 is a schematic diagram of the master computer controlling all the operations.

In FIG. 4 a schematic diagram of the master computer (14) is shown. It includes a processor (41), a RAM memory (42), a ROM memory (43) and a plurality of connections with the different mechanical and electronic functions of the system: the control of the movement of the inspected objects (44), the control of the X-ray sources and detectors (45, 46) and a connection with the image acquisition system (47) which comprises the SIT image detectors. Other I/O devices (48, 49) are connected either directly or remotely to the process (41).

The processor (41) may be a microprocessor such as is found in the IBM PS/2 Personal Computer, or be a host processor connected to the other components through a data link.

The master computer (14) is suitably programmed to control the correct 3D positioning of the apparatus and the frame grabbing. The program will be stored in the RAM (42). Further the RAM (42) will contain information regarding the kind of inspection to be performed, the geometry of the sources and the detectors and appropriate calibration information.

The images captured by the system according to the present invention could be processed and analysed using techniques well known to those skilled in the art. The U.S. Pat. No. 4,926,452, for example, explains some of these techniques.

We claim:

1. An X-ray inspection apparatus for electronic circuits comprising:
   means for directing X-rays to produce X-ray images representing illuminations of circuit elements from different angles; and
   detecting means for detecting said images;
   said inspection being characterized in that said detecting means comprises a plurality of detectors, each of said detectors positioned to intercept X-rays after passing through a circuit element from a particular associated angle of illumination, and said detectors being:
   disposed symmetrically about an axis orthogonal to the plane in which the illuminated circuit element lies,
   radially movable with respect to said axis, and
   laterally movable along said axis.

2. The system of claim 1 wherein said means for directing X-rays comprise a plurality of X-ray sources.

3. The system of claim 2, wherein said X-ray sources are disposed symmetrically about said axis and are radially movable with respect to said axis and laterally movable along said axis.

4. The system of claim 1 wherein each of said X-ray detectors comprises a Silicon Intensified Target image detector.

5. The system of claim 1 further comprising image processing means for combining images from the detectors to form a single composite image.

6. The system of claims 2, 3, 4 or 5 further comprising control means for changing the relative positions of said means for directing X-rays, said electronic circuit and said X-ray detectors so that the angle of incidence of the X-rays can be varied without changing the magnification value.

7. An X-ray inspection apparatus for electronic circuits comprising:
   means for directing X-rays to produce X-ray images representing illuminations of circuit elements from different angels, said means comprising a plurality of X-ray sources disposed symmetrically about said axis, said X-ray sources being radially movable with respect to said axis and laterally movable along said axis; and detecting means for detecting said images;

said inspection apparatus being characterized in that said detecting means comprises a plurality of detectors, each of said detectors positioned to intercept X-rays after passing through a circuit element from a particular associated angle of illumination.

* * * * *